(12) United States Patent
Rosten et al.

(10) Patent No.: US 7,316,318 B1
(45) Date of Patent: *Jan. 8, 2008

(54) SUSPENSION PACKAGE

(75) Inventors: David Rosten, Cambridge, MN (US); Tad Kinyon, Elysian, MN (US); Chris Osborn, Germantown, WI (US)

(73) Assignee: Perfecseal, Inc., Oshkosh, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/050,203

(22) Filed: Feb. 3, 2005

Related U.S. Application Data

(62) Division of application No. 10/141,090, filed on May 7, 2002, now Pat. No. 6,889,839.

(51) Int. Cl.
*B65D 81/02* (2006.01)

(52) U.S. Cl. .................. 206/583; 206/363; 206/438

(58) Field of Classification Search ............. 206/363, 206/364, 438–440, 466, 467, 493, 583
See application file for complete search history.

(56) References Cited

U.S. PATENT DOCUMENTS

| | | | |
|---|---|---|---|
| 2,837,208 A * | 6/1958 | Lingenfelter | ............... 206/583 |
| 4,065,816 A | 1/1978 | Sawyer | |
| 4,155,453 A | 5/1979 | Ono | |
| 4,491,225 A * | 1/1985 | Baillod | ....................... 206/583 |
| 4,606,460 A | 8/1986 | Luray | |
| 4,697,703 A | 10/1987 | Will | |
| 4,903,827 A | 2/1990 | Phelps et al. | |
| 5,056,665 A | 10/1991 | Boecker et al. | |
| 5,183,159 A * | 2/1993 | Hojnacki et al. | ........... 206/583 |
| 5,405,000 A | 4/1995 | Hagedon et al. | |
| 5,405,005 A | 4/1995 | White | |
| 5,590,778 A | 1/1997 | Dutchik | |
| 5,720,391 A | 2/1998 | Dohm et al. | |
| 5,769,235 A | 6/1998 | Keach et al. | |
| 6,006,917 A | 12/1999 | Loeffler | |
| 6,161,695 A | 12/2000 | Nicolais | |
| 6,622,864 B1 * | 9/2003 | Debbs et al. | ............... 206/438 |
| 6,915,901 B2 | 7/2005 | Feinberg et al. | |

OTHER PUBLICATIONS

Packaging World, Jan. 2001, p. 40, 42 "Redesign Puts Twist Into Hip Trays" by Rick Lingle.

* cited by examiner

*Primary Examiner*—Luan K Bui
(74) *Attorney, Agent, or Firm*—Bemis Company, Inc.

(57) ABSTRACT

The invention is directed to a suspension package that is used to support and protect sensitive articles such as prosthetics and other medical implants when such articles are being shipped. The suspension package is comprised of a pouch, and a tray member and a cover member. The pouch is designed to be connected to and suspended between the tray member and the cover member. During shipping, the tray member and the cover member protect the packaged article to prevent damage. The pouch includes apertures around its perimeter that allow the pouch to be attached to suspension posts of the tray member. The suspension posts are tapered and include detent grooves that are designed to stretch and retain the pouch to prevent movement during shipping.

27 Claims, 4 Drawing Sheets

US 7,316,318 B1

SUSPENSION PACKAGE

The present application is a divisional of U.S. patent application Ser. No. 10/141,090, which was filed on May 7, 2002 and issued on May 10, 2005 under U.S. Pat. No. 6,889,839.

BACKGROUND OF THE INVENTION

The present invention relates to packaging for protecting and supporting sensitive articles such as prosthetics and other medical implants when such articles are shipped from manufacturer to medical center. The suspension package is designed to maintain the sterility of the medical implants as they are shipped. Typically the devices are sterilized at the OEM and generally not resterilized at the hospital. The suspension package is designed to be relatively inexpensive to produce and allows for easy removal of medical implants from the packaging during surgery.

Prior art packages used to protect sensitive articles during shipping have many shortcomings. First, they involve a tray-in-tray system that creates a need for many separate types of trays involving both extensive warehouse storage for the various sizes and shapes and tooling costs of $20,000 to $50,000 for each separate size and shape. Second, the prior art packages involve foam pieces or other inserts to hold the devices and these inserts are both labor intensive to use and can produce foreign particulate matter in the operating room which is extremely undesirable. Third, they do not adequately protect the article during shipping. This allows damage to occur, rendering the medical implant unusable. Lastly, the prior art packaging does not allow for easy removal of the medical implants from the packing.

A need has arisen for an improved design for a suspension package. The present invention discloses an improved design for packaging sensitive articles that safely protects the articles during shipping and storage, is less expensive to produce and package, allows articles to be sterilized before shipment and allows for easy removal of articles from the packaging by the medical staff during an operating procedure.

SUMMARY OF THE INVENTION

The disclosed suspension package effectively protects sensitive articles, such as electronics, prosthetics and other devices, during shipping that are sensitive to impacts and vibration, to prevent damage. The suspension package is comprised of a pouch, a semi-rigid tray member and a cover member. The pouch is designed to contain and support an article to be packaged and is sealed to enclose the article. The preferred embodiment of the pouch includes a plurality of apertures positioned around its perimeter to allow attachment to one or both of the cover members. The preferred embodiment of the tray member includes a central recess with a surrounding flange that includes a plurality of outwardly extending tapered posts. The tapered posts further include detent grooves located near the base of the posts to engage and retain the pouch. In one embodiment, the cover member is also a semi-rigid structure and also includes a central recess with a raised flange. The raised flange includes a plurality of recesses adapted to engage the tapered posts when the package is assembled. The pouch, when positioned in the tray, is suspended under moderate tension above the central recesses and between the tray member and the cover member, which provides a buffer of air between the tray and cover members. Since the pouch is suspended between the tray and cover members, any impact to the suspension package will not contact the packaged article.

DETAILED DESCRIPTION OF THE PREFERRED EMBODIMENT

Figure 1:
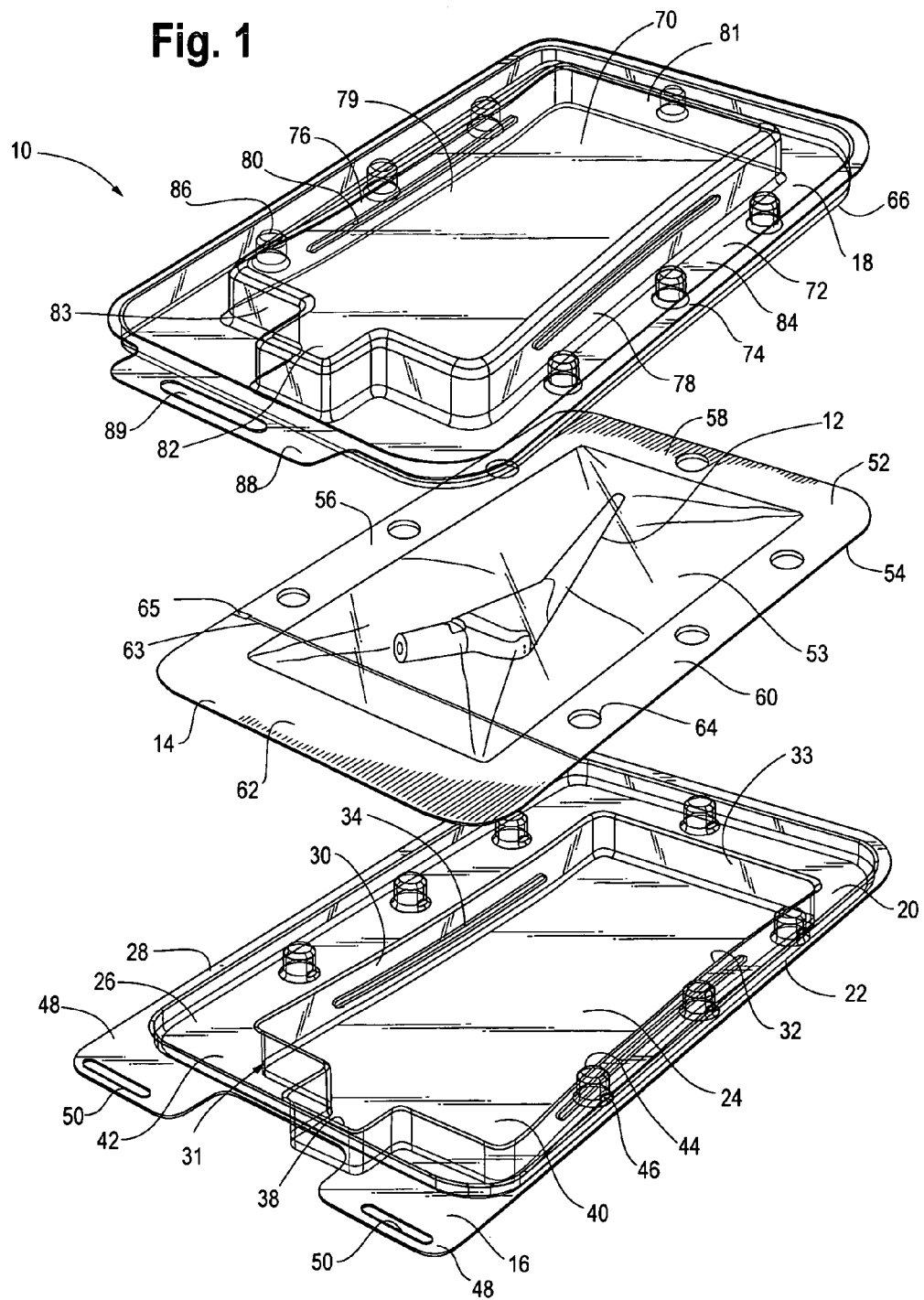
FIG. 1 is an exploded view of the suspension package of the present invention.

For the purpose of promoting an understanding of the principles of the invention, references will be made to the embodiments illustrated in the drawings. Specific language will also be used to describe the same. It will, nevertheless, be understood that no limitation of the scope of the invention is thereby intended, such alterations and further modifications in the illustrated device, and such further applications of the principles of the invention illustrated herein being contemplated as would normally occur to one skilled in the art to which the invention relates.

The embodiment shown in FIG. 1 is directed to a suspension package 10 for sensitive articles 12, such as prosthetics and other medical implants, and is designed to prevent damage to the articles 12 during shipping and storage. The suspension package 10 is also designed to prevent contamination of the articles 12 by placing them in a heat sealable pouch 14 so that they are ready for immediate use without any additional sterilization or preparation needed.

The suspension package 10 includes a tray member 16, the suspension pouch 14 and a cover member 18. The tray member 16 and the cover member 18 encapsulate the suspension pouch 14 to protect the article 12 from damage. In this embodiment the tray member 16, the cover member 18 and the pouch 14 are all preferably formed from transparent materials which allows medical personnel involved in the implant procedure to visually ensure that they have the correct implant hardware prior to opening the suspension package in the surgical room.

The tray member 16 of the suspension package 10 includes an inside surface 20 and an outside surface 22 and can be made from polyethylene terephthalate (PET) or other thermoformable semi-rigid plastics known to those skilled in the art. The inside surface 20 is adapted to contain and support the pouch 14 and includes a central recess 24, a surrounding flange 26, and a lip 28 around the perimeter. The outside surface 22 is the backside of the inside surface 20 and protects the pouch 14 from damage.

The central recess 24 is shown as being rectangular in shape and includes four side walls 30, 31, 32 and 33 and a bottom surface 40. Any shape recess designed to accommodate the article 12 may be used. First and second side walls 30 and 32 are inwardly curved along the length of the wall and include outwardly extending ribs 34, shown in FIG. 3, extending parallel to the length of the sidewalls 30 and 32. During surgery, surgeons and their staff are outfitted with sterilized operating clothing, including surgical gloves. The inwardly curved shape of the sidewalls and the ribs 34 of the first and second side walls 30 and 32 are designed to allow medical staff, wearing surgical gloves, to easily grasp the tray member 16 allowing the separation of the tray member 16 from the cover member 18 and thereby providing access to the suspension pouch 14.

Figure 3:
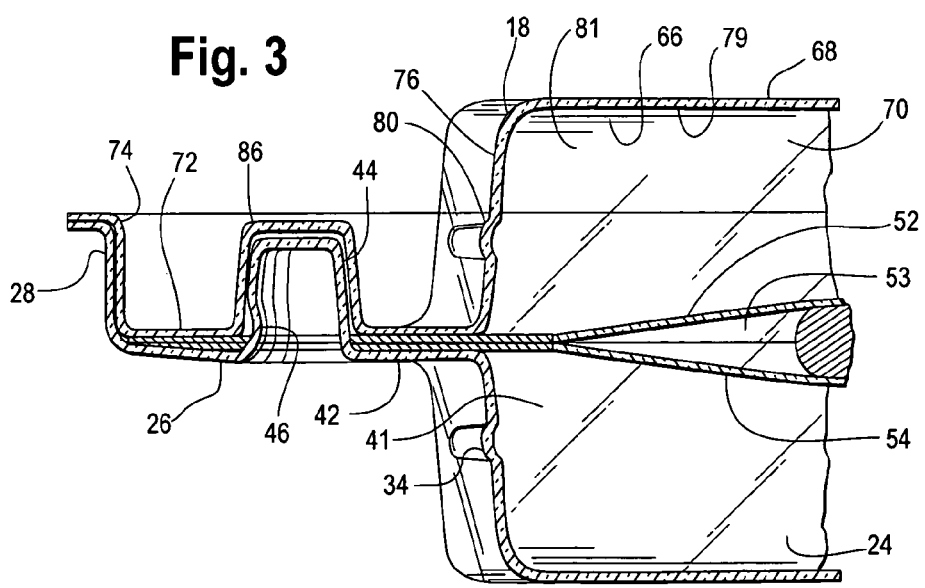
FIG. 3 is a sectional view of a portion of the suspension package, taken along sectional line 3-3 of FIG. 2.

The central recess 24 also includes a depression 38, as shown in FIG. 1. The depression 38 aids in the removal of the pouch 14 from the tray member 16 when wearing surgical gloves. The depression 38 allows the medical staff to position their fingers beneath the pouch 14 so that they can grasp the pouch 14 and separate it from the tray member 16. A bottom surface 40 of the central recess 24 is spaced below the surrounding flange 26 so that when the pouch 14 is installed, an air gap 41, shown in FIG. 3, is created between the pouch 14 and the bottom surface 40. The air gap 41 creates a buffer zone to protect the contents of the pouch 14 in the event that the central recess 24 is deformed due to an impact during shipping.

Figure 2:
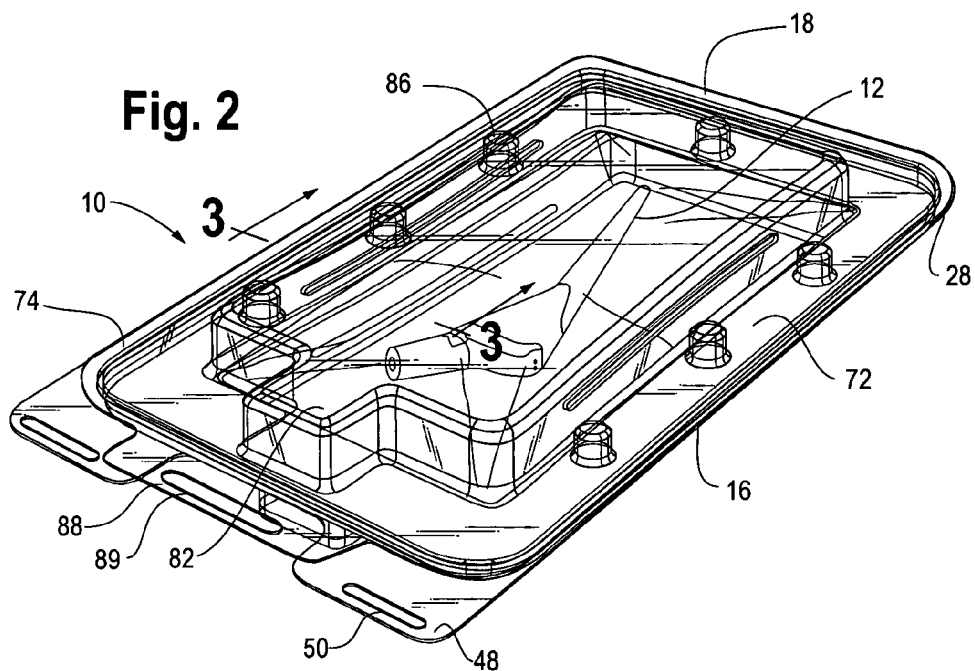
FIG. 2 is a perspective view of an assembled suspension package.

The flange 26, shown in FIGS. 1 and 3, surrounds the central recess 24 and is positioned vertically above the surface 40 and extends outwardly therefrom. The flange 26 includes a deck 42 that lies in a plane generally parallel to the plane formed by the bottom surface 40 of the central recess 24 but positioned vertically above it. The flange 26 includes a plurality of tapered suspension posts 44 extending upwardly from the deck 42 to allow for the attachment of the suspension pouch 14. The suspension posts 44 taper outwardly from top to bottom as they approach the deck 42 of the flange 26. The taper of the suspension posts 44 allows the suspension pouch 14 to be stretched when installed over the posts, creating tension across the pouch 14. The suspension posts 44 further include detent grooves 46 at their base. The detent grooves 46 lock the suspension pouch 14 in position at the base of the posts 44 to maintain the position of the pouch 14 during shipping. The suspension posts 44 illustrated in FIGS. 1-3 are evenly spaced around three sides of the central recess 24 to ensure uniform tension across the pouch 14.

The lip 28 surrounds the flange 26 forming the outer and upper edge of the tray member 16, and is best shown in FIGS. 1 and 3. The lip 28 is adapted to engage and retain a corresponding lip on the cover member 18 when assembled and aids in providing rigidity to the tray member 16 to prevent flexing. The lip 28 includes a pair of tabs 48 that include traction ribs 50. The tabs 48 aid in separating the tray member 16 and the cover member 18 to facilitate easy removal of the packaged article 12.

The suspension pouch 14, best shown in FIGS. 1 and 3, is preferably formed from first and second film layers 52 and 54. The film is a barrier type film, which presents a high barrier to both oxygen and moisture, such as aluminum oxide coated biaxially oriented polyester (OPET) adhesively laminated to biaxially oriented nylon which is itself adhesively laminated to a heat sealant.

Preferably the aluminum oxide coated OPET is positioned as the outside or exterior layer, with the oxide coating to the inside, bonded against the middle layer of biaxially oriented nylon.

To the extent that any printing is placed on the pouch, such printing should be on the nylon layer to avoid damage to the aluminum oxide coated OPET.

Other films and laminations with sufficient barrier for the particular purpose could also be used with this innovation so long as the material used has sufficiently high strength to allow it to maintain integrity following the vacuum sealing process and the rigors of transport in a suspended state. The first and second film layers 52 and 54 are heat sealed along three edges 56, 58 and 60 to form a product receiving chamber 53 into which the product to be shipped is inserted. Alternatively a single sheet of film may be folded over on itself and sealed around the edges. The article 12 is sterilized, using traditional sterilization methods after being sealed within the pouch 14. Once the article 12 is placed within the pouch 14, it can be heat sealed along a fourth edge 62. Optionally, the pouch 14 can be vacuum sealed and then heat sealed along the fourth edge 62 to prevent shifting of the contents in the pouch. In some situations it might be beneficial to seal the entire area of the pouch surrounding the article to limit the ability of the article to shift within the pouch. The pouch may also include a score line 63, best illustrated in FIG. 1, with a tear notch 65 to aid in opening the pouch 14. Optionally the material from which the pouch is made could include a peelable component as known to those of ordinary skill in the packaging art to facilitate opening of the pouch in the sterile operating field. Another alternative is to heat seal the entire pouch 14 up to and around the packaged article 12 to prevent unwanted movement. The pouch 14 includes a plurality of apertures 64 positioned around the perimeter of the pouch 14 so as to receive the upwardly extending extension posts 44 to allow the pouch 14 to be attached over the suspension posts 44 of the tray member 16. When the pouch 14 is attached to the tray member 16, the edge of the apertures 64 engage and are retained by the detent grooves 46 to prevent movement of the pouch 14 during shipping and storage. The apertures 64 are sized slightly smaller than the base diameter of the suspension posts 44 so that when the pouch 14 is attached to the posts 44, the first and second film layers 52 and 54 are stretched, applying tension to the pouch 14.

The cover member 18 of the suspension package 10 of this embodiment includes an inside surface 66 and an outside surface 68, as shown in FIG. 3. The cover member 18 can also be formed from a semi-rigid thermoplastic such as polyethylene terephthalate (PET). The inside surface 66 includes a central recess 70, a surrounding flange 72 and a lip 74 around its periphery as shown in FIG. 1.

The central recess 70, shown in FIGS. 1 and 3 of the cover member 18, is illustrated as being rectangular in shape and includes a first side wall 76, a second side wall 78, a third side wall 81, a fourth side wall 83, and a bottom surface 79. The first and second side walls 76 and 78 are curved inwardly along their length in the same manner as the side walls 30 and 32 and include outwardly extending ribs 80 extending parallel to the length of the sidewalls 76 and 78. The concave shape of the side walls 76 and 78 and the ribs 80 are designed to allow medical staff, wearing surgical gloves, to easily grasp the cover member 18 allowing the separation of the tray member 16 from the cover member 18, thereby providing access to the suspension pouch 14. The central recess 70 also includes a depression 82 of similar size and shape to the depression 38. The depression 82 provides an opening to aid in removal of the pouch 14 from the cover members 16 and 18 when wearing gloves. The depression 82 allows the medical staff to position their fingers beneath the pouch 14 so that they can grasp the pouch 14 and separate it from the cover members 16 and 18. The bottom surface 79 of the central recess 70 is spaced apart from the surrounding flange 72 so that when the tray member 16 and the pouch 14 are connected with the cover member 18, an air gap 81 is created between the pouch 14 and the bottom surface 79, as shown in FIG. 3. The air gap 81 creates a buffer zone to protect the contents of the pouch 14 in the event that the central recess 70 is deformed due to an impact during shipping.

The flange 72 surrounds the central recess 70 and includes a deck 84 that lies in a plane generally parallel to the plane formed by the bottom surface 79 of the central recess 70, but positioned vertically below it as shown in FIG. 1. The flange 72 includes a plurality of recesses 86 surrounding the central recess 70 and adapted to accept the suspension posts 44 of the tray member 16. The recesses 86 are arranged so that when the tray member 16 and the cover member 18 are connected, the suspension posts 44 and the recesses 86 align, as shown in FIG. 3.

The lip 74, shown in FIGS. 1 and 3, surrounds the flange 72 and forms the outer edge of the cover member 18 and is adapted to engage the lip 28 of the tray member 16 when assembled. The lip 74 aids in providing rigidity to the cover member 18 to prevent flexing. The lip 74 includes a central tab 88 that includes a traction groove 89. The tab 88 aids in separating the tray member 16 and the cover member 18 to facilitate easy removal of the packaged article 12.

The article 12 is packaged by first forming a pouch 14 from film layers 52 and 54, creating a product receiving chamber 53 and creating apertures 64 along the outer edge of the pouch 14. Once the pouch 14 is formed, the article 12 is placed in the pouch 14, and the pouch is placed on the suspension posts 16 by positioning the apertures 64 of the pouch 14 over the suspension posts 44 and moving the pouch downwardly where the edges of the apertures 64 are locked into position by the detent grooves 46. The pouch is then air evacuated and heat sealed to enclose the receiving chamber 53. Once the pouch 14 is sealed, the cover member 18 is positioned over it and is connected to the tray member 16 by lowering the recesses 86 over the suspension posts 44 to encapsulate the pouch 14 to prevent damage to the article 12 therein.

Figure 4:
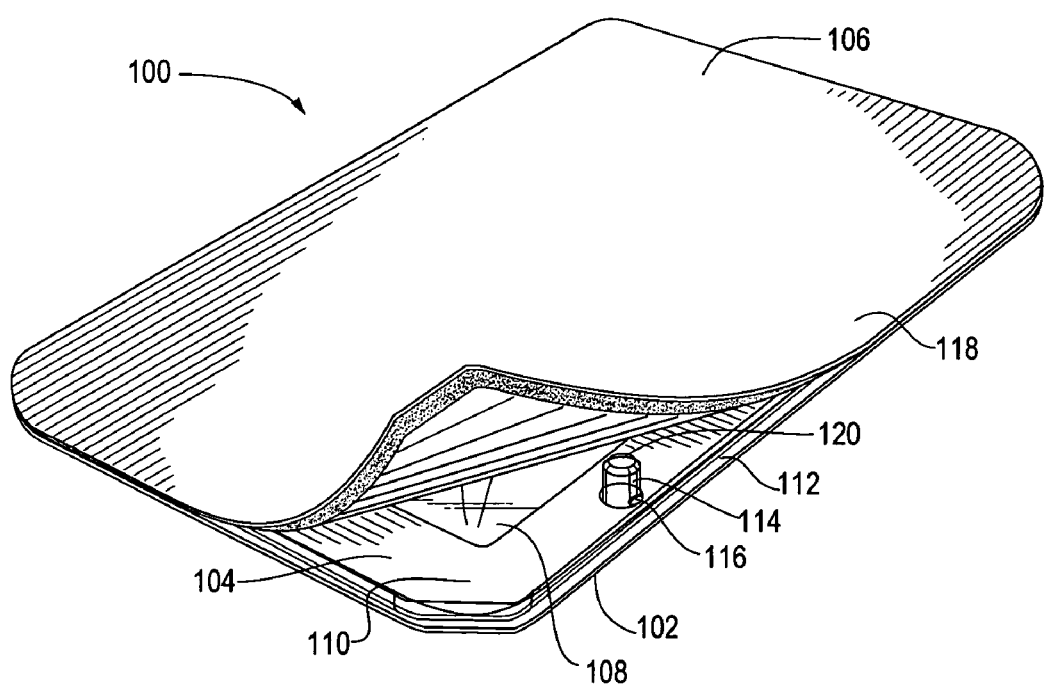
FIG. 4 is a perspective view of a second embodiment of the suspension package in accordance with the invention showing a portion of the cover member peeled away.

The second embodiment of the suspension package 100, shown in FIG. 4, includes a tray member 102, a suspension pouch 104 and a cover member 106. This embodiment eliminates a formed semi-rigid cover and allows for ethylene oxide sterilization of the article by using gas permeable materials for at least one side of the pouch as well as the cover of the tray.

The tray member 102 of the second embodiment 100 is similar to the tray member 16 of the first suspension package embodiment 10 in that it includes a central recess 108 and a surrounding flange 110, but differs by incorporating a wider lip 112. The wider lip 112 provides a sealing surface so the cover member 106 can be sealed to the lip 112. The flange 110 of the tray member 102 includes a plurality of elongated, tapered, upwardly extending suspension posts 114. The suspension posts 114 on the second embodiment are longer than those on the tray member 16 so as to increase the spacing between the pouch 104 and the cover member 106 when the package is assembled. The suspension posts 114 have an upper surface 120 that lies in the same plane as the lip 112 so that the lip 112 and the upper surface 120 of the suspension posts 114 have the same elevation. This allows the cover member 106 to be secured to both the suspension posts 114 and the lip 112 when the cover member 106 is installed. The suspension posts 114 are adapted to engage and retain the suspension pouch 104 in the same manner as the embodiment of FIGS. 1-3. The tapered sides of the of the suspension posts 114 are designed to create tension on the suspension pouch 104 to restrict the movement of the pouch 104 and its contents during shipping. The suspension posts 114 include detent grooves 116 to prevent disengagement of the suspension pouch 104 from the suspension posts 114 during shipping.

The preferred type of pouch for this embodiment utilizes a breathable material such as heat sealable Tyvek® spun bonded polyolefin or paper which provide a barrier against contaminants and damage but allow the passage of sterilization gas to sterilize the packaged article 12 for one or both surfaces of the pouch.

The cover member 106 may be fabricated from lid stock such as heat sealable Tyvek® spun-bonded olefin or paper, which also provides a barrier against contaminants and damage to the packaged article 12 yet allows the passage of sterilization gas. The cover member 106 is attached to the tray member 102 by heat sealing the edges 118 of the cover 106 to the lip 112. The cover member 106 is also heat sealed to the upper surface 120 of the suspension posts 114 to provide extra strength to the cover member 106 and to retain the suspension pouch 104 to the posts 114 in the event the pouch 104 becomes disengaged from the detent grooves 116. The use of the cover member 106 in place of the cover member 18 reduces packaging weight and minimizes production costs.

Figure 5:
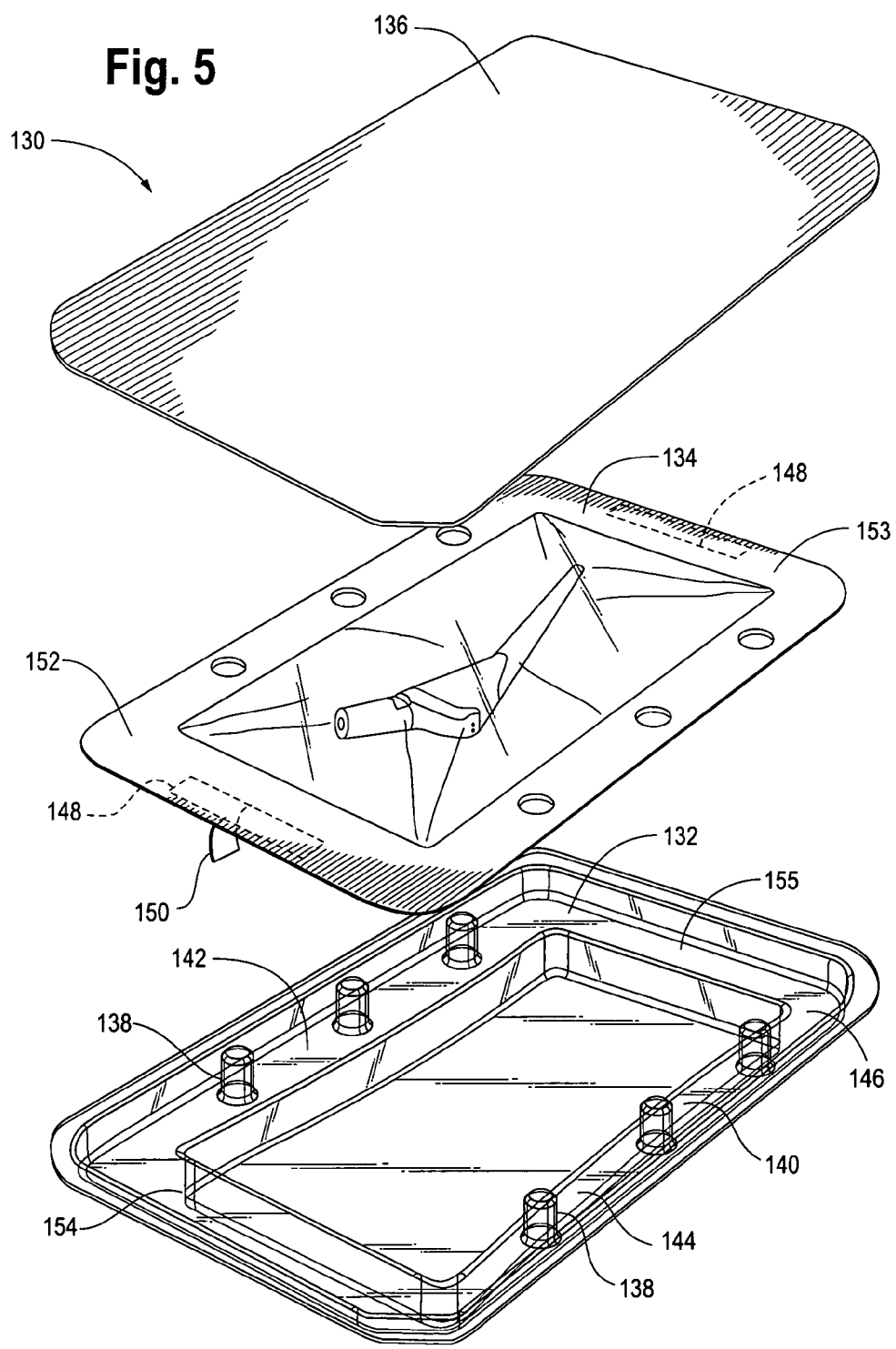
FIG. 5 is an exploded view of a third embodiment of the suspension package in accordance with the invention.

The third embodiment of the suspension package 130, shown in FIG. 5, includes a tray member 132, a suspension pouch 134 and a cover member 136. The tray member 132 is similar to the second suspension package embodiment 100, shown in FIG. 4, with the exception that the tray member 132 includes suspension posts 138 along only two sides 142 and 144 of the flange 140. No end posts, as shown in FIG. 1, are present in this embodiment. To secure the pouch 134 of the tray member 132, an adhesive strip 148 with a pull-off release liner 150 is placed along first and second ends 152 and 153 of the pouch 134 to secure the pouch 134 to a third and a fourth side 154 and 155 of the flange 140.

For some packaging situations, the tray member 132 can be designed without suspension posts 138. The suspension pouch 134 would be outfitted with additional adhesive strips 148 so that one would be placed on each side of the pouch 134 as well as the ends 152 and 153. With this arrangement, the pouch 134 is adhered to the deck 146 to prevent its movement during shipping. It should be understood that the adhesive can be applied either to the pouch or to the deck 146. This embodiment eliminates posts which makes it more versatile as well as making it easier to load the pouch into the tray in certain situations.

Various features of the invention have been particularly shown and described in connection with the illustrated embodiment of the invention, however, it must be understood that these particular arrangements merely illustrate, and that the invention is to be given its fullest interpretation within the terms of the appended claims.

The invention claimed is:

1. A suspension package for protecting and supporting an article comprising:

a pouch adapted to contain and support the article, said pouch having a first layer connected at its outer edge to a second layer to form a product receiving chamber therebetween, said pouch including a plurality of apertures positioned on the perimeter of said pouch;

a tray member having a recess defining a pouch receiving chamber with a flange surrounding said recess, said recess having at least two curvilinear side walls;

a plurality of outwardly extending tapered posts extending from said flange, said posts including detent grooves adapted to engage and retain the edges of said apertures of said pouch;

a cover member adapted to be connected to said tray member wherein said pouch receiving chamber is suspended between said cover member and said tray member to prevent damage to the article within said pouch receiving chamber.

2. The suspension package of claim 1, wherein said pouch containing the article is sealed to enclose said product receiving chamber.

3. The suspension package of claim 1, wherein said tray member includes a tab to aid in the separation of said tray member from said cover member.

4. The suspension package of claim 1, wherein said at least two curvilinear side walls of said recess include at least one traction rib.

5. The suspension package of claim 1, wherein said cover member includes a tab to aid in the separation of said cover member from said tray member.

6. The suspension package of claim 1, wherein said first and second pouch layers are formed from a barrier film.

7. The suspension package of claim 6, wherein said barrier film is selected from the group of films consisting of EVOH, PE and PP.

8. The suspension package of claim 1 wherein said tray member includes a first lip along an outer edge of said flange, said first lip adapted to engage and retain said cover member.

9. The suspension package of claim 1 wherein said cover member includes a second lip along an outer edge of said raised rim, said second lip adapted to engage and retain said first lip of said tray member.

10. The suspension package of claim 1, wherein said cover member includes a central recess with at least two curvilinear side walls, said cover member further having a rim with a plurality of recesses adapted to receive said posts.

11. A suspension package for protecting and supporting an article comprising:
a pouch adapted to contain and support the article, said pouch having a first film layer connected at an outer edge to a second film layer to form a product receiving chamber, said pouch including a plurality of apertures positioned along two edges of said pouch;
a tray member having a first recess and a second recess positioned within said first recess, said first recess having a surrounding flange with outwardly extending posts, said posts adapted to engage said apertures of said pouch, and said flange having a lip above said flange;
means for retaining said pouch to said tray member, said retaining means limited to elements on said tray member and created create tension across said pouch and to prevent movement of said pouch with respect to said tray member; and a cover member secured to said lip.

12. The suspension package of claim 11 wherein said cover member is heat sealed to said tray member.

13. The suspension package of claim 11 wherein said pouch containing the article is sealed to enclose said product receiving chamber.

14. The suspension package of claim 11 wherein said first and second film layers are formed from a barrier film.

15. The suspension package of claim 14 wherein said barrier film is selected from the group of films consisting of EVOH, PE and PP.

16. The suspension package of claim 11 wherein said pouch includes a tear notch and a score line to aid in the opening of said pouch.

17. The suspension package of claim 11, wherein said retaining means is in the form of an adhesive layer.

18. The suspension package of claim 17, wherein said adhesive layer is adapted to be adhered to said surrounding flange of said first recess and to said pouch to secure said pouch to said tray member.

19. A suspension package for protecting and supporting an article comprising:
a pouch adapted to contain and support the article, said pouch having a first layer connected to a second layer at their outer edges to form a product receiving chamber therebetween;
a tray member having a first recess, a flange surrounding said first recess, a lip above said flange, and a second recess positioned within said first recess to receive said pouch and article;
means for securing said pouch to said tray member to create tension across said pouch and to limit movement of said pouch within said second recess, wherein said means for securing are limited to elements on said tray member; and
a cover member secured to said lip, wherein the article is supported between said tray member and said cover member to prevent damage to the article.

20. The suspension package of claim 19, wherein said pouch is sealed to enclose the article within said product receiving chamber.

21. The suspension package of claim 19, wherein said first and second pouch layers are formed from barrier film.

22. The suspension package of claim 21, wherein said barrier film is selected from the group of films consisting of EVOH, PE and PP.

23. The suspension package of claim 21, wherein said barrier film is aluminum oxide coated oriented polyester, laminated to biaxially oriented nylon, laminated to a heat sealable polymeric layer.

24. The suspension package of claim 19, wherein said cover member is secured to said tray member by heat sealing.

25. The suspension package of claim 19, wherein said cover member is secured to said tray member by use of an adhesive.

26. The suspension package of claim 19, wherein said securing means is in the form of an adhesive that secures said pouch to said tray member.

27. The suspension package of claim 19, wherein said securing means is in the form of a plurality of suspension posts that are adapted to engage and retain said pouch.

* * * * *

UNITED STATES PATENT AND TRADEMARK OFFICE
CERTIFICATE OF CORRECTION

| | | |
|---|---|---|
| PATENT NO. | : 7,316,318 B1 | Page 1 of 1 |
| APPLICATION NO. | : 11/050203 | |
| DATED | : January 8, 2008 | |
| INVENTOR(S) | : David Rosten et al. | |

It is certified that error appears in the above-identified patent and that said Letters Patent is hereby corrected as shown below:

In the Claims

In column 7, line 50, in claim 11, delete "created create" and insert -- creating --.

In column 7, line 50 and 51, in claim 11, delete "to prevent" and insert -- preventing --.

Signed and Sealed this
Fifteenth Day of March, 2016

Michelle K. Lee
*Director of the United States Patent and Trademark Office*